US011448875B2

(12) United States Patent
Chen (10) Patent No.: US 11,448,875 B2
(45) Date of Patent: Sep. 20, 2022

(54) METHOD, SYSTEM AND CONTROL DEVICE FOR CONTROLLING DISPLAY OF AUGMENTED REALITY DEVICE, AND AUGMENTED REALITY DEVICE

(71) Applicant: BOE TECHNOLOGY GROUP CO., LTD., Beijing (CN)

(72) Inventor: Yanjun Chen, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 708 days.

(21) Appl. No.: 16/338,521

(22) PCT Filed: Nov. 9, 2018

(86) PCT No.: PCT/CN2018/114680
§ 371 (c)(1),
(2) Date: Apr. 1, 2019

(87) PCT Pub. No.: WO2019/205575
PCT Pub. Date: Oct. 31, 2019

(65) Prior Publication Data
US 2021/0373326 A1 Dec. 2, 2021

(30) Foreign Application Priority Data
Apr. 25, 2018 (CN) .......................... 201810378477.1

(51) Int. Cl.
*G06F 3/01* (2006.01)
*G06T 19/00* (2011.01)
(Continued)

(52) U.S. Cl.
CPC .......... *G02B 27/0101* (2013.01); *A61B 3/066* (2013.01); *G02B 27/0093* (2013.01);
(Continued)

(58) Field of Classification Search
CPC ..... A61B 3/066; G02B 27/0093; G06F 3/013; G06K 9/00617; G06T 19/006; G06T 2219/2012
See application file for complete search history.

(56) References Cited

U.S. PATENT DOCUMENTS

2006/0203102 A1* 9/2006 Yang ........................ H04N 9/73
348/225.1
2007/0236656 A1 10/2007 Jeong et al.
(Continued)

FOREIGN PATENT DOCUMENTS

CN 103778602 A 5/2014
CN 103870148 A 6/2014
(Continued)

OTHER PUBLICATIONS

First Office Action for Chinese Patent Application No. 201810378477.1 dated Jul. 3, 2019.
(Continued)

*Primary Examiner* — Grace Q Li
(74) *Attorney, Agent, or Firm* — Calfee, Halter & Griswold LLP (57) ABSTRACT

Disclosed is a control device querying a preset data set to obtain color vision sensitivity information corresponding to acquired identity information of a user of the augmented reality device; the control device judging whether the user is a color recognition disorder patient according to obtained color vision sensitivity information; the control device acquiring a personalized color display mode corresponding to the color vision sensitivity information as a target color display mode when the user is judged as a color recognition disorder patient; and the control device providing the augmented reality device with the target color display mode so that the augmented reality device employs the target color display mode to display an image.

17 Claims, 5 Drawing Sheets

(51) Int. Cl.
  *G06V 40/18*   (2022.01)
  *G02B 27/01*   (2006.01)
  *A61B 3/06*    (2006.01)
  *G02B 27/00*   (2006.01)

(52) U.S. Cl.
  CPC ........... *G02B 27/017* (2013.01); *G06F 3/013* (2013.01); *G06T 19/006* (2013.01); *G06V 40/197* (2022.01); *G02B 2027/0178* (2013.01); *G06T 2219/2012* (2013.01)

(56) References Cited

U.S. PATENT DOCUMENTS

| | | | |
|---|---|---|---|
| 2015/0192776 A1* | 7/2015 | Lee | G09B 21/008 |
| | | | 345/690 |
| 2016/0033772 A1* | 2/2016 | Han | H04N 1/6083 |
| | | | 359/630 |
| 2017/0076697 A1 | 3/2017 | Zhou | |
| 2017/0330376 A1* | 11/2017 | Haseltine | G06F 3/011 |
| 2019/0166343 A1* | 5/2019 | Anders | G06F 9/4451 |
| 2020/0150828 A1* | 5/2020 | Kim | G06F 3/0416 |

FOREIGN PATENT DOCUMENTS

| | | |
|---|---|---|
| CN | 103929605 A | 7/2014 |
| CN | 205510304 U | 8/2016 |
| CN | 106488219 A | 3/2017 |
| CN | 106504713 A | 3/2017 |
| CN | 106782385 A | 5/2017 |
| CN | 108563023 A | 9/2018 |
| KR | 20070099969 A | 10/2007 |

OTHER PUBLICATIONS

Search Report and Written Opinion for International Application No. PCT/C2018/114680 dated Jan. 28, 2019.

* cited by examiner

METHOD, SYSTEM AND CONTROL DEVICE FOR CONTROLLING DISPLAY OF AUGMENTED REALITY DEVICE, AND AUGMENTED REALITY DEVICE

RELATED APPLICATION

The present application is the U.S. national phase entry of PCT/CN2018/114680, with an international filling date of Nov. 9, 2018, which claims priority to the Chinese patent application No. 201810378477.1 filed on Apr. 25, 2018, the entire disclosure of which is hereby incorporated by reference in its entirety.

FIELD

The present disclosure relates to the technical field of displays, and particularly to a method, system and control device for controlling display of an augmented reality device, and an augmented reality device.

BACKGROUND

Augmented Reality (AR) technology, as a visual enhancement technology, may calculate position and angle of real-world images captured by a camera or a user in real time, and correspondingly merge computer-simulated information such as virtual images, videos or sounds into the real world, and allow interacting therewith. As computing capabilities of the Central Processing Unit (CPU), Graphics Processing Unit (GPU) and supercomputer improve progressively, augmented reality technology is increasingly applied to various industries. For example, in the field of education, augmented reality technology may provide users with a special learning space to visualize abstract content to be learned; in the medical field, augmented reality technology may be used to assist doctors in performing accurate positioning during a surgical procedure; in the military field, simulated training may be performed through augmented reality technology; in the field of games or entertainment, real combat feeling is virtualized through the augmented reality technology.

However, in the related art, if a color recognition disorder patient employs an AR system, it will occur that the AR information cannot be recognized, thereby reducing the user's experience in use.

SUMMARY

In one aspect, the present disclosure provides a method for controlling display of an augmented reality device. In an exemplary embodiment, the method comprises: a control device querying a preset data set to obtain color vision sensitivity information corresponding to acquired identity information of a user of the augmented reality device; the control device judging whether the user is a color recognition disorder patient according to the obtained color vision sensitivity information; the control device acquiring a personalized color display mode corresponding to the color vision sensitivity information as a target color display mode when the user is judged as a color recognition disorder patient; and the control device providing the augmented reality device with the target color display mode so that the augmented reality device employs the target color display mode to display an image.

In an exemplary embodiment, before querying, the method further comprises: the control device acquiring the user's identity information collected by the augmented reality device; and the control device querying to determine whether the preset data set comprises the collected user's identity information. When the collected user's identity information is comprised, the control device queries the preset data set to obtain the color vision sensitivity information corresponding to the collected user's identity information.

In an exemplary embodiment, the method further comprises: the control device initiating a color vision sensitivity test on the user when the collected user's identity information is not comprised in the preset data set, so as to obtain the color vision sensitivity information corresponding to the user's identity information. The control device judges whether the user is a color recognition disorder patient based on the color vision sensitivity information resulting from the test. The control device stores the collected user's identity information in association with the color vision sensitivity information resulting from the test into the data set.

In an exemplary embodiment, before providing the augmented reality device with the target color display mode, the method further comprises: acquiring ambient brightness information and user's visual field environment color information detected by the augmented reality device; generating a compensation parameter for each sub-pixel in an image according to the color vision sensitivity information, the ambient brightness information and the user's visual field environment color information; performing compensation for a data signal of each sub-pixel according to the compensation parameter of each sub-pixel, and generating a compensated data signal; and providing the compensated data signal together with the target color display mode to the augmented reality device so that the augmented reality device employs the target color display mode to display the image based on the compensated data signal.

In an exemplary embodiment, generation of a compensation parameter for each sub-pixel comprises: the control device generating a data signal target value for each pixel in the image, according to the color vision sensitivity information, the ambient brightness information and the user's visual field environment color information. Each pixel comprises a plurality of sub-pixels. The control device generates a compensation parameter for each sub-pixel according to the data signal target value of each pixel.

In an exemplary embodiment, acquirement of a personalized color display mode corresponding to the color vision sensitivity information comprises: the control device instructing the augmented reality device to output a plurality of options for personalized color display modes corresponding to the color vision sensitivity information, to enable the user to determine whether the plurality of options comprise a personalized color display mode desired by the user. If yes, a personalized color display mode determined by the user is acquired. If no, the control device instructs the augmented reality device to output another plurality of options for personalized color display modes corresponding to the color vision sensitivity information, for the user to continue to perform the determining step.

In an exemplary embodiment, the method further comprises: when the user is not judged as a color recognition disorder patient, the control device acquires a standardized color display mode corresponding to the color vision sensitivity information as the target color display mode.

In another aspect, the present disclosure provides a control device. In an exemplary embodiment, the control device comprises a query device configured to query a preset data set to obtain color vision sensitivity information corresponding to acquired identity information of a user of an augmented reality device; a judger configured to judge, according to obtained color vision sensitivity information, whether the user is a color recognition disorder patient; and a color mode acquirer configured to, when the judger judges that the user is a color recognition disorder patient, acquire a personalized color display mode corresponding to the color vision sensitivity information as a target color display mode, and provide the augmented reality device with the target color display mode so that the augmented reality device employs the target color display mode to display an image.

In an exemplary embodiment, the query device is further configured to acquire the user's identity information collected by the augmented reality device, query to determine whether the preset data set comprises the collected user's identity information, and when the collected user's identity information is comprised, query the preset data set to obtain the color vision sensitivity information corresponding to the collected user's identity information.

In an exemplary embodiment, when the collected user's identity information is not comprised, the query device initiates a color vision sensitivity test on the user, to obtain the color vision sensitivity information corresponding to the user's identity information; and the judger is further configured to judge whether the user is a color recognition disorder patient based on the color vision sensitivity information resulting from the test.

In an exemplary embodiment, the control device further comprises a storage module configured to store the preset data set, and store the collected user's identity information in association with the color vision sensitivity information resulting from the test into the data set.

In an exemplary embodiment, the control device further comprises a compensator configured to generate a compensation parameter for each sub-pixel in the image according to the color vision sensitivity information and ambient brightness information and user's visual field environment color information detected by the augmented reality device; perform compensation for a data signal of each sub-pixel according to the compensation parameter of each sub-pixel to generate a compensated data signal; and provide the compensated data signal together with the target color display mode to the augmented reality device, so that the augmented reality device employs the target color display mode to display an image based on the compensated data signal.

In an exemplary embodiment, the color mode acquirer is further configured to, when the judger judges that the user is not a color recognition disorder patient, acquire a standardized color display mode corresponding to normal color display as the target color display mode.

In a further aspect, the present disclosure provides an augmented reality device. In an exemplary embodiment, the augmented reality device comprises a display configured to display an image in a color display mode; and a display mode setter configured to set a color display mode for the display, the color display mode comprising at least one personalized color display mode in a case where a user of the augmented reality device is a color recognition disorder patient and a standard color display mode in a case where the user is a normal color recognizer. The display mode setter is configured to receive a target color display mode from a control device and set it as a color display mode for the display. The target color display mode corresponds to color vision sensitivity information of the user of the augmented reality device.

Optionally, an exemplary embodiment of the augmented reality device further comprises an identity information acquirer configured to collect user's identity information, and provide the collected user's identity information to the control device, so that the control device, based on the collected user's identity information, queries for the color vision sensitivity information corresponding thereto.

In an exemplary embodiment, the augmented reality device further comprises a detector configured to detect ambient brightness information and user's visual field environment color information, and provide the detected information to the control device so that the control device generates a compensated data signal for each sub-pixel of the image based on the color vision sensitivity information and the ambient brightness information and the user's visual field environment color information. The display is further configured to employ the received target color display mode to display the image based on the compensated data signal.

In an exemplary embodiment, the detector comprises an ambient brightness sensor configured to sense the ambient brightness information; and a visual field environment color sensor configured to sense the user's visual field environment color information.

In an exemplary embodiment, the augmented reality device includes augmented reality glasses as a body. The augmented reality glasses comprise a glasses frame and lenses disposed on the glasses frame. The display, the display mode setter, the identity information acquirer and the detector are all placed on the glasses frame.

In a further aspect, the present disclosure provides an augmented reality processing system, comprising: the control device and the augmented reality device as described above.

In a further aspect, the present disclosure provides an augmented reality device. The augmented reality device comprises: the control device as described above and a display for displaying an image in a color display mode. The color mode acquirer sets the color display mode for the display based on the target color display mode.

In a further aspect, the present disclosure provides a computer storage medium. The computer storage medium comprises instructions which, when executed by a processor, enable the processor to implement the method as described above.

BRIEF DESCRIPTION OF THE DRAWINGS

The above and other aspects of the present disclosure will now be described in more detail with reference to figures which illustrate exemplary embodiments.

DETAILED DESCRIPTION

In order to enable those skilled in the art to better understand the technical solutions of the present disclosure, an augmented reality processing method, system, and control device and an augmented reality device provided by the present disclosure are described in detail below with reference to the figures. In the following description, for purpose of illustration not limitation, certain specific details of exemplary embodiments of the present disclosure are described to enable clear and thorough understanding of the present disclosure. However, those skilled in the art should easily appreciate that without seriously departing from the spirit and scope of the present disclosure, that the present disclosure may be implemented according to other embodiments which do not precisely comply with details stated in the text herein. In addition, in this context, for purpose of brevity and clarity, detailed description of well-known devices, circuits, and methods are omitted in order to avoid redundant details and possible confusion.

The reason why the human eye has color vision is because three different types of cones are distributed on the retina, and are sensitive to red, green and blue primary color bands of the visible spectrum, respectively. After retina cells are stimulated by light, light information received by the three different types of cells is converted into electrical signals which are transmitted to the brain for fusion processing, thereby enabling people to obtain a color distinguishing capability. Modern neurophysiological studies have found that pigments of each type of cone absorb certain wavelengths under light illumination and reflect light of some other wavelengths. The pigments of each type of cone are different in sensitivity to different parts of the spectrum, i.e., they have different spectral absorption curves.

Color recognition disorder means that loss or dysfunction of one or more types of cones in the human eye causes a symptom of inability to distinguish a certain color, some or all colors in the natural spectrum. For example, if two or more types of cones are missing, total color blindness will be caused, that is, the patient only has monochromatic perception. If the photosensitive spectrum of one or more types of cones translates or gets incomplete, color weakness will be caused. All of these may lead to a reduction in the patient's color distinguishing capability.

In general, color recognition disorder may comprise color blindness or color weakness. Color blindness may comprise total color blindness or partial color blindness, and partial color blindness may comprise red blindness, green blindness or yellow-blue blindness. The color weakness may comprise total color weakness or partial color weakness, and partial color weakness may comprise red weakness, green weakness or yellow-blue weakness. As is known, there may be many kinds of color recognition disorders.

The color vision sensitivity information may be used to identify the type of color recognition disorder or to identify the user as having no color recognition disorder, namely, a normal color recognizer. In other words, the color recognition disorder patient and the normal color recognizer may be distinguished by acquiring the color vision sensitivity information. For example, when the color vision sensitivity information identifies that the user develops red blindness, the user is judged as a red blindness patient. In an exemplary embodiment, the color vision sensitivity information may comprise the sensitivity of each type of cones to the visible spectrum.

According to an exemplary embodiment, it allows providing a color recognition disorder patient with a personalized color display mode different from a standard color display mode, namely, performing color correction, so as to enable the color recognition disorder patient to easily recognize the information displayed by the augmented reality device, thereby greatly improving the user's experience.

Figure 1:
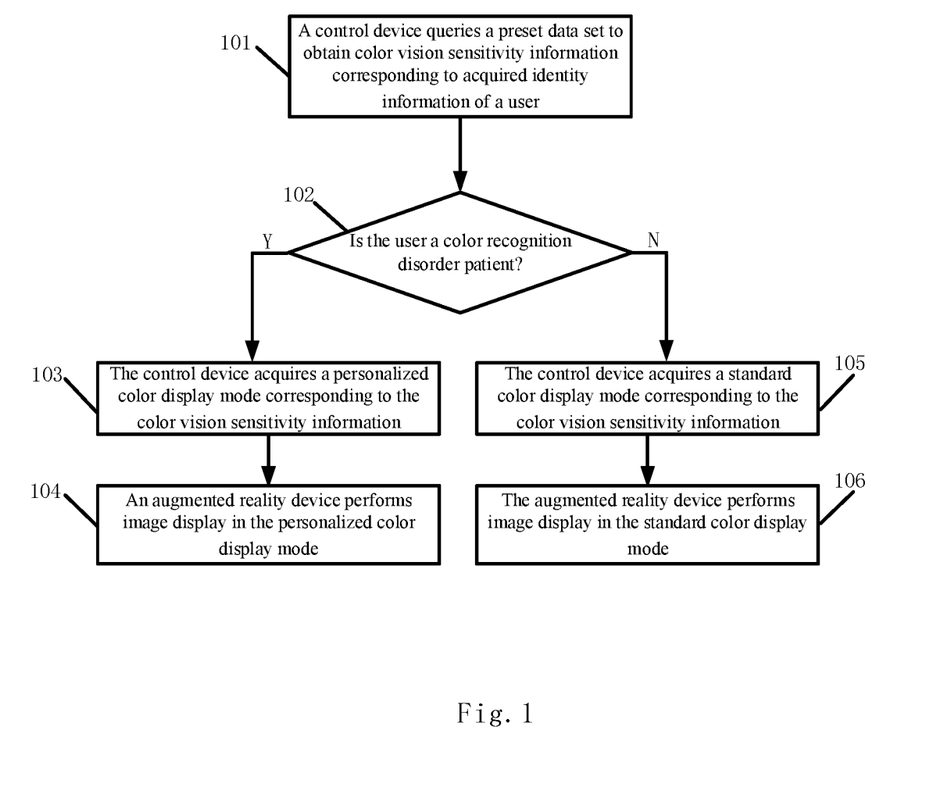
FIG. 1 is a flowchart of an augmented reality processing method according to an exemplary embodiment.

FIG. 1 is a flowchart of a method for display of an augmented reality device according to an exemplary embodiment. As shown in FIG. 1, the method comprises the following steps.

Step 101: a control device queries a preset data set to obtain color vision sensitivity information corresponding to acquired identity information of a user. This user is a user of the augmented reality device. In an embodiment, the control device may acquire the user's biometric data from the augmented reality device, including but not limited to iris information, face information and fingerprint information, etc. Alternatively, or additionally, the control device may also obtain a user identifier of the user, such as a username, from the augmented reality device.

In an exemplary embodiment, the data set may be pre-set by the user registering with the control device or the augmented reality device. For example, the data set may be pre-set by collecting identity information and corresponding color vision sensitivity information input by the user when he/she registers as a user of the augmented reality device. Additionally, the data set may also be updated each time a new user uses the augmented reality device. The pre-set data set may be stored locally in the control device or may be stored on a remote device accessible by the control device.

Step 102: the control device judges whether the user is a color recognition disorder patient according to the color vision sensitivity information corresponding to the user's identity information (namely, as obtained). The color vision sensitivity information may comprise the sensitivity of the user's each type of cones to the visible spectrum. It is possible to judge whether the user is a color recognition disorder patient and/or determine a degree of the color recognition disorder according to the sensitivity of each type of cones to the visible spectrum. For example, if the color vision sensitivity information indicates that the user is less sensitive to the red region of the spectrum, the user might be a red blindness patient.

Step 103: if it is determined in step 102 that the user is a color recognition disorder patient, the control device acquires a personalized color display mode corresponding to the color recognition disorder indicated by the color vision sensitivity information as a target color display mode. In an embodiment, different color recognition disorder types may correspond to different personalized color display modes. In these personalized color display modes, it is possible to improve color distinguishing conditions of the color recognition disorder patient by color correction such as differential coloring and color filtering, or by associating unrecognizable colors with other visual indicators such as cross-hatching. Exemplarily, a red blindness color display mode corresponding to a red blindness user may be to correct red to a color which is close to read and recognizable by the user.

Step 104: the control device provides the personalized color display mode (namely, a target color display mode adapted for the color recognition disorder of the user) to the augmented reality device so that the augmented reality device is enabled to perform image display using the personalized color display mode, and the process ends. In an exemplary embodiment, the control device may transmit a control command comprising the personalized color display mode to the augmented reality device to instruct the augmented reality device to perform image display in accordance with the personalized color display mode. In this step, the AR image display may be performed in the personalized color display mode.

Step 105: if it is determined in step 102 that the user is not a color recognition disorder patient, the control device acquires a standardized color display mode that renders a normal color as the target color display mode. The standardized color display mode is a color display mode in which color correction for the color recognition disorder is not performed.

Step 106: the control device provides the standardized color display mode to the augmented reality device so that the augmented reality device performs image display in the standardized color display mode, and the process ends. In this step, display of an AR image may be performed in the standardized color display mode.

In the method for display of the augmented reality device provided by an exemplary embodiment of the present disclosure, if the control device judges that the user is a color recognition disorder patient according to the color vision sensitivity information, the augmented reality device is controlled to employ a respective personalized color display mode corresponding to respective color recognition disorders to display images, avoiding the situation that the color recognition disorder patient cannot recognize the AR information, and thereby improving the user's experience in use.

The operations of the above exemplary embodiment may be further described with reference to one or more logic flows. It may be appreciated that a typical logic flow does not necessarily have to be performed in a given order or in any particular order unless otherwise indicated. Moreover, various activities described with respect to the logic flow may be performed in a serial or parallel manner. The logic flow may be implemented by using one or more hardware units and/or software units of the described exemplary embodiment, or replacement units as desired by a given design and performance constraint group. For example, the logic flow may be implemented as logic (e.g., computer program instructions) for execution by a logical device (e.g., a general-purpose or special-purpose computer).

Figure 2:
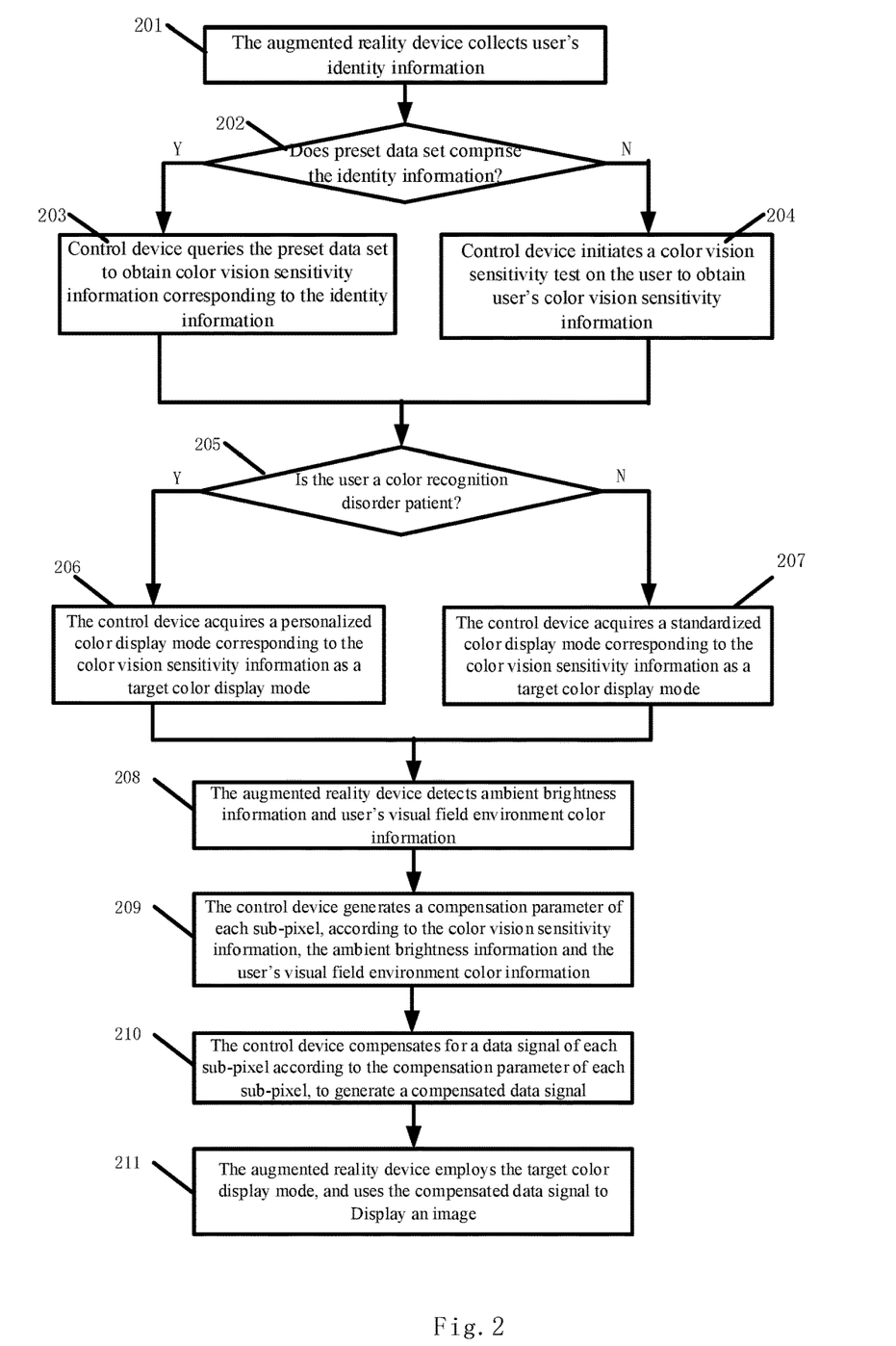
FIG. 2 is a flowchart of another augmented reality processing method according to an exemplary embodiment.

FIG. 2 is a flowchart of another method according to an exemplary embodiment. As shown in FIG. 2, the method comprises the following steps.

Step 201: the augmented reality device collects user's identity information. In an exemplary embodiment, the user's identity information may comprise the user's iris information. Since each user's iris information is different, each user's iris information may be used to uniquely identify the user's identity. Alternatively, the collected user's identity information may also comprise other types of biometric data of the user, including but not limited to fingerprints, faces, and the like.

Step 202: the control device acquires the user's identity information collected by the augmented reality device, and queries to determine whether a preset data set comprises the collected identity information.

In an exemplary embodiment, a data set may be preset, and identity information of different users is stored in the data set. For example, the user's identity information may be collected each time the user uses the augmented reality device, and the collected user's identity information is stored in the data set. Alternatively, the user may be pre-registered before iii the user uses the augmented reality device, so that the user's identity information is stored in the data set. Exemplarily, iris information sampling may be performed for the user multiple times through the iris recognition technology to acquire the user's iris information, and the collected user's iris information is stored into the data set as the user's identity information. Optionally, the data set may comprise multiple types of identity information corresponding to a certain user.

The query may comprise comparing the collected identity information with identity information stored in the data set. When identity information matching the collected identity information exists in the data set, it is determined that the data set comprises the user's identity information.

Step 203: if it is determined in step 202 that the preset data set already comprises the collected identity information, the control device queries for the color vision sensitivity information corresponding to the collected identity information from the preset data set.

Color vision sensitivity information of different users may also be stored in the preset data set, and each piece of color vision sensitivity information corresponds to respective user's identity information. In an exemplary embodiment, color vision sensitivity information of different users may be acquired in advance or result from a test, and color vision sensitivity information of different users is stored in the data set.

Step 204: if it is determined in step 202 that the data set does not comprise the collected identity information, the control device may initiate a color vision sensitivity test on the user to obtain the user's color vision sensitivity information. The color vision sensitivity test may comprise a quantitative test of the user's image color differentiating capability.

In some exemplary embodiments, the control device may perform the color vision sensitivity test by means of the augmented reality device. The augmented reality device may display a picture of a color vision test chart to the user for color vision sensitivity test. The picture of the color vision test chart may be an AR display picture. When viewing the picture of the color vision test chart, the user may provide feedback on the picture of the color vision test chart via touch or speech. The test result about the color vision sensitivity may be determined based on the feedback. The augmented reality device outputs the test result to the control device, and the control device gets the user's color vision sensitivity information according to the test result.

In practical applications, optionally, the control device may also display the picture of the color vision test chart via other display devices, and determine the test result based on the user's feedback on the picture of the color vision test chart. The control device gets the user's color vision sensitivity information according to the test result.

In practical applications, optionally, a hue test method may also be employed to test the color vision sensitivity information. For example, the color vision sensitivity information is tested and got by performing a Munsell hue test. The control device acquires the color vision sensitivity information resulting from the test.

Optionally, the control device may store the collected user's identity information in association with the user's color vision sensitivity information got from the color vision test into the data set.

Step 205: the control device judges whether the user is a color recognition disorder patient according to the color vision sensitivity information.

In an exemplary embodiment, whether the user is a color recognition disorder patient may be judged based on the sensitivity of each cone cell comprised in the color vision sensitivity information to the visible spectrum. Furthermore, the type and degree and the like of the color recognition disorder of the user may be judged based on the color vision sensitivity information.

Step 206: if the user is a color recognition disorder patient, the control device acquires a personalized color display mode corresponding to the color vision sensitivity information as a target color display mode.

Exemplarily, a personalized color display mode corresponding to the type and optionally the degree of the color recognition disorder corresponding to the color vision sensitivity information may be acquired.

Step 207: if the user is not a color recognition disorder patient, i.e., he is a normal color recognizer, the control device acquires a standardized color display mode corresponding to normal color display as the target color display mode.

The color display mode of the augmented reality device comprises a standardized color display mode and one or more personalized color display modes. For users who do not develop the color recognition disorder, namely, normal color recognition users, image display may be performed in a standardized color display mode. For a user with color recognition disorder, image display may be performed in a personalized color display mode.

Both the standardized color display mode and the personalized color display mode may be preset. A corresponding personalized color display mode may be set for each type of color recognition disorder. In an exemplary embodiment, the personalized color display mode may be implemented by establishing a gamma curve which is applied for display and corresponds to a different type of color recognition disorder. In an embodiment, the personalized color display modes may be achieved by pre-learning color display effects desired by patients with different types of color recognition disorders. As such, for example, if the color recognition disorder is determined to be red blind, the personalized color display mode corresponding to the red blind may be acquired from the preset personalized color display modes. In the personalized color display mode corresponding to the red blind, appropriate color correction is performed for the red color, and that mode is adapted for use when the image is displayed for a red blind patient.

In some exemplary embodiments, considering that color recognition disorder patients or other individuals might have higher response sensitivity and faster response speed to certain colors, or personal preferences for certain colors, a personalized color display mode may further be a color display mode in which colors are autonomously selected and collocated.

In some application fields of an augmented reality device, color collocation is crucial in merging virtually-displayed content and the real world. For example, in the process of real-scene navigation using augmented reality technology, especially in the vehicle-mounted field, when colors of the foreground (virtually-displayed content) and the background (visual field environment) are highly coincident or similar, it is difficult to distinguish the virtually-displayed content or the time for distinguishing may increase because of reduction of the contrast. If, at this time, a user is traveling at a high speed, an accident is extremely probably caused. Therefore, it might be desirable to perform real-time color compensation in conjunction with ambient brightness, ambient color, and user's color recognition capability.

In some exemplary embodiments, a method according to exemplary embodiments of the present disclosure may further comprise the following steps.

Step 208: the augmented reality device detects ambient brightness information and user's visual field environment color information. The ambient brightness information and the user's visual field environment color information may all be information detected in real time.

Step 209: the control device generates a compensation parameter for each sub-pixel in an image to be displayed, according to the color vision sensitivity information, the ambient brightness information and the user's visual field environment color information.

In an exemplary embodiment, the control device may generate a data signal target value for each pixel in the image, based on one or more of the color vision sensitivity information, the ambient brightness information and the user's visual field environment color information. Each pixel comprises a plurality of sub-pixels. For example, each pixel may comprise a red (R) sub-pixel, a green (G) sub-pixel, and a blue (B) sub-pixel.

The control device may generate a compensation parameter for each of its sub-pixels based on the data signal target value of each pixel.

Step 210: the control device compensates for the data signal of each sub-pixel according to the compensation parameter of each sub-pixel, to generate a compensated data signal.

Exemplarily, the compensation parameter for each sub-pixel may be added up with the data signal of each sub-pixel to derive the compensated data signal for each sub-pixel. In some embodiments, the brightness of each sub-pixel of the red sub-pixel, green sub-pixel and blue sub-pixel may be adjusted by compensating for the sub-pixel's data signal.

Step 211: the augmented reality device employs a target color display mode, and uses the compensated data signal to display an image, and the process ends. Color correction of the image may be achieved by displaying the image using the compensated data signal.

It may be appreciated that steps 208-211 are optional. In some exemplary embodiments, the augmented reality device may directly perform image display after receiving the target color display mode from the control device.

In the method provided by exemplary embodiments, if a user is judged as a color recognition disorder patient according to color vision sensitivity information, the augmented reality device performs image display using a personalized color display mode corresponding to the color vision sensitivity information. This avoids the situation that a color recognition disorder patient cannot recognize the AR information, and may effectively improve the sensory experience of different individuals and the accuracy of information recognition, thereby improving the user's experience in use.

In addition, in the exemplary embodiment, color compensation correction of a displayed image is implemented based on color vision sensitivity information, ambient brightness information and user's visual field environment color information, thereby effectively avoiding the situation that the colors of foreground and background cannot be distinguished at certain moments, which is caused by changes of the user's visual field color with the real environment during use, and thereby mitigating or even avoiding obstacles and confusion in user's observation.

Figure 3:
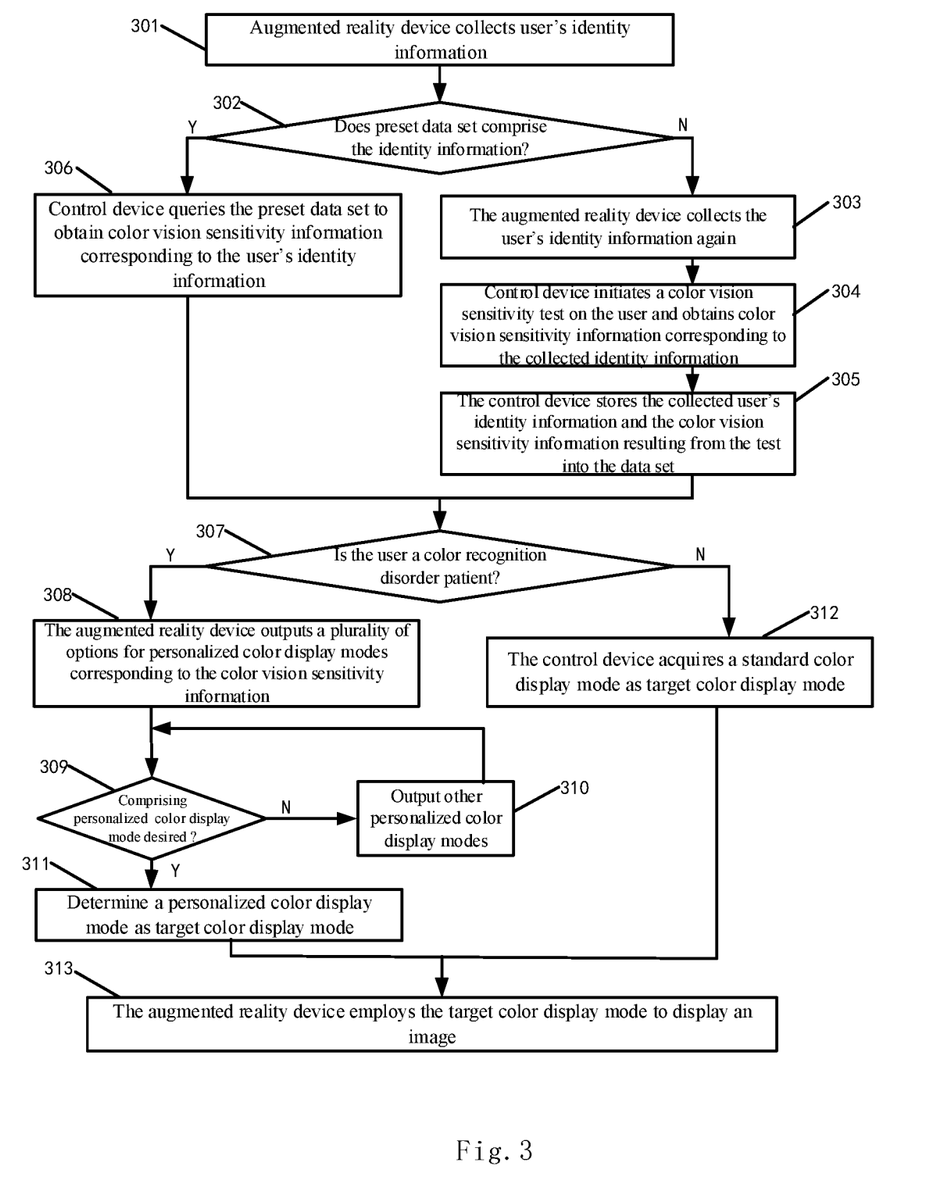
FIG. 3 is a flowchart of a further augmented reality processing method according to an exemplary embodiment.

FIG. 3 is a flowchart of a further method according to an exemplary embodiment. As shown in FIG. 3, the method comprises the following steps.

Step 301: the augmented reality device collects the user's identity information. The user's identity information may comprise the user's iris information.

Step 302: the control device queries and determines whether a preset data set comprises the collected identity information.

Step 303: if it is determined that the preset data set does not comprise the collected identity information, the augmented reality device collects the user's identity information again.

Exemplarily, the iris recognition technique may be employed to perform iris sampling several times to collect multiple samples of the user's iris. In an embodiment, if it is determined that the preset data set does not comprise the collected identity information, the user is prompted to perform iris information collection multiple times. The collected user's iris information is stored as the user's identity information. It enables embodiments to accurately collect the iris samples by implementing re-collection of the iris information.

Step 304: the control device initiates a color vision sensitivity test on the user to get color vision sensitivity information corresponding to the collected identity information. For example, a standard color blindness test may be performed on the user to test his color recognition capability and color vision sensitivity. Alternatively, the control device may directly acquire input of the color vision sensitivity information from the user. In an embodiment, the control device may present a plurality of options about color recognition disorder to the user on the user interface, and acquires the user's selection of a relevant option to get the color vision sensitivity information corresponding to the user. Exemplarily, the presented options may comprise: normal color vision, red blindness/weakness, green blindness/weakness, yellow-blue blindness/weakness, and the like. Additionally, the presented options may further comprise: performing a color vision test and initiating the color vision test when the user selects the option of performing a color vision test.

Step 305: the control device may store the collected user's identity information in association with the got color vision sensitivity information into the data set.

Step 306: if it is determined in step 302 that the data set already comprises the user's identity information, the control device queries the color vision sensitivity information corresponding to the user's identity information from the preset data set.

Step 307: the control device judges, according to the got or queried color vision sensitivity information, whether the user is a color recognition disorder patient. In some embodiments, the color vision sensitivity information comprises the sensitivity of each type of cones to the visible spectrum. Whether the user is a color recognition disorder patient may be judged according to the sensitivity of each type of cones to the visible spectrum.

Step 308: when it is judged in step 307 that the user is a color recognition disorder patient, the augmented reality device may output a plurality of options for personalized color display mode corresponding to the color vision sensitivity information. Each option may correspond to a different color collocation scheme.

In an exemplary embodiment, the control device outputs a control instruction to the augmented reality device for controlling the augmented reality device to display a color mode picture corresponding to each option, the color mode picture being an AR display picture. Optionally, the augmented reality device may output a color mode picture, which comprises a plurality of options for the personalized color display mode corresponding to the color vision sensitivity information.

Step 309: whether a personalized color display mode desired by the user is comprised in the plurality of options is judged.

In an exemplary embodiment, a specific color mode picture corresponding to each option may be presented to the user, a user's feedback on each color mode picture may be received, and judgment may be performed based on the feedback. In some embodiments, the feedback may be a rating of the user's satisfaction degree with colors of each color mode picture. Exemplarily, assuming a maximum rating is 10, when the received feedback indicates that the user's rating of one or more color mode pictures reaches or exceeds a rating threshold (e.g., 8), it may be judged that the color display mode corresponding to the color mode picture is the personalized color display mode desired by the user. When the user's rating of all color mode pictures does not reach the rating threshold, it may be judged that the plurality of options do not comprise the personalized color display mode desired by the user. In other exemplary embodiments, the feedback may also be a simple "yes" or "no". When the received feedback is "yes", it indicates that the color mode picture is desired by the user, and when the received feedback is "no", it indicates that the user cannot accept the color mode picture. The user may provide the feedback through an input device (including but not limited to a key, a touch pad and microphone, etc.) of the control device or the augmented reality device. Exemplarily, when viewing the color mode picture, the user may indicate that the plurality of options comprise a personalized color display mode desired by the user by touching a color display mode option corresponding to the color mode picture to his satisfaction.

Step 310: if it is judged that the plurality of options do not comprise the personalized color display mode desired by the user, the control device outputs, through the augmented reality device, another plurality of options for personalized color display modes corresponding to the color vision sensitivity information, for the user to select, and continues to perform step 309.

When the user is dissatisfied with all the given personalized color display modes, an exemplary embodiment outputs a new personalized color display mode for the user to continue to select.

Optionally, a new color mode picture may be output, and the new color mode picture comprises another plurality of options for the personalized color display modes corresponding to the color vision sensitivity information.

Step 311: if it is judged that plurality of options already comprise the personalized color display mode desired by the user, the augmented reality device outputs the personalized color display mode desired by the user to the control device, and the control device determines a personalized color display mode as a target color display mode based on the personalized color display mode desired by the user.

Step 312: when it is judged in step 307 that the user is not a color recognition disorder patient, the control device acquires a standardized color display mode as the target color display mode.

Step 313: the augmented reality device performs image display by using the target color display mode, and the process ends.

As would be appreciated, after determining the target color display mode, compensation may be performed according to the data signal shown in steps 208-211 in FIG. 2, and the compensated data signal may be used for image display.

Figure 4:
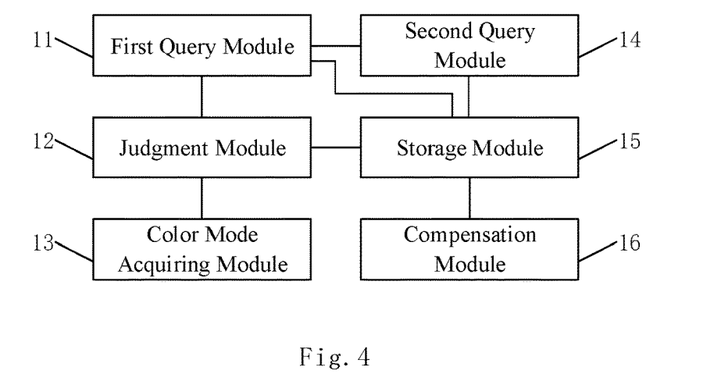
FIG. 4 is a schematic structural diagram of a control device according to an exemplary embodiment.

In an exemplary embodiment, the user is allowed to select a personalized color display mode autonomously, thereby adapting to the situation in which an individual user has high sensitivity and fast response speed to certain colors, and has personal preferences to certain colors. FIG. 4 is a schematic structural diagram of a control device according to an embodiment of the present disclosure. As shown in FIG. 4, the control device comprises: a first query module 11, a judgment module 12, and a color mode acquiring module 13.

The first query module 11 is configured to query a preset data set to obtain color vision sensitivity information corresponding to acquired identity information of the user. The judgment module 12 is configured to judge, according to the color vision sensitivity information corresponding to the user's identity information, whether the user is a color recognition disorder patient. The color mode acquiring module 13 is configured to, when the judgment module 12 judges that the user is a color recognition disorder patient, obtain a personalized color display mode corresponding to the color vision sensitivity information as a target color display mode, and provide the augmented reality device with the target color display mode so that the augmented reality device employs the target color display mode to display an image.

Furthermore, the control device further comprises: a second query module 14. The second query module 14 is configured to acquire the user's identity information collected by the augmented reality device. The second query module 14 is further configured to query to determine whether the preset data set comprises the user's identity information collected by the augmented reality device. If it is determined that the preset data set comprises the collected identity information, the first query module 11 is triggered to use the acquired identity information to query the preset data set to obtain the color vision sensitivity information corresponding to the collected user identity information.

Furthermore, if the second query module 14 determines that the preset data set does not comprise the user's identity information, it may instruct/trigger the augmented reality device to collect the user's identity information again. Additionally, or alternatively, in this case, the first query module 11 may initiate a color vision sensitivity test on the user. For example, the first query module 11 may instruct/trigger the augmented to reality device to perform the color vision sensitivity test, comprising displaying the color vision test chart and receiving the user's feedback on the color vision side view.

It may be appreciated that the first and second query modules 14 may be separate query modules or may be implemented by an integrated query module.

The control device further comprises a storage module 15. The storage module 15 is configured to store the data set. The storage module 15 may store the user's identity information collected by the augmented reality device in association with (namely, in one-to-one correspondence with) the color vision sensitivity information corresponding to the user's identity information and resulting from the test into the data set. The first query module 11 may acquire the data set from the storage module 15 so as to query the user's color vision sensitivity information based on the identity information.

The judgment module 12 may receive the queried color vision sensitivity information from the first query module 11 or color vision sensitivity information resulting from the test and perform judgment as to whether the user is a color recognition disorder patient based thereon.

Furthermore, the control device further comprises: a compensation module 16. The compensation module 16 is configured to generate a compensation parameter for each sub-pixel in the image according to the color vision sensitivity information and ambient brightness information and user's visual field environment color information detected by the augmented reality device; perform compensation for the data signal of each sub-pixel according to the compensation parameter of each sub-pixel to generate a compensated data signal, and provide the compensated data signal together with the target color display mode to the augmented reality device so that the augmented reality device employs a personalized color display mode to display an image based on the compensated data signal.

Furthermore, the color mode acquiring module 13 is further configured to, when the judgment module 12 judges that the user is not a color recognition disorder patient, obtain a standardized color display mode corresponding to normal color display as the target color display mode, so that the augmented reality device employs the standard color display mode to display an image.

In an exemplary embodiment, the control device may be a computer.

The control device provided by the embodiment selects a personalized color display mode corresponding to color vision sensitivity information for image display of an augmented reality device when a user is determined as a color recognition disorder patient according to the color vision sensitivity information, thereby avoiding the situation that the color recognition disorder patient cannot recognize the AR information, and thereby improving the user's experience in use.

Figure 5:
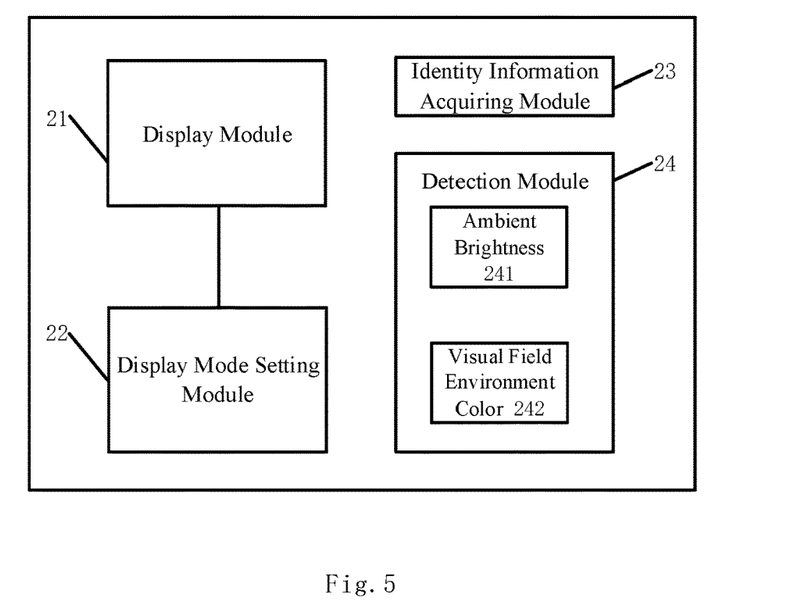
FIG. 5 is a schematic structural diagram of an augmented reality device according to an exemplary embodiment.

FIG. 5 is a schematic structural diagram of an augmented reality device according to an exemplary embodiment. The augmented reality device may be used with a control device in accordance with an exemplary embodiment, such as a control device described in connection with FIG. 4. As shown in FIG. 5, the augmented reality device comprises a display module 21 and a display mode setting module 22.

The display module 21 is configured to display an image in a color display mode.

The display mode setting module 22 is configured to set a color display mode for the display module 21, the color display mode comprising at least one personalized color display mode in a case where the user of the augmented reality device is a color recognition disorder patient and a standard color display mode in a case where the user is a normal color recognizer. The display mode setting module 22 is configured to receive a target color display mode from the control device and set a color display mode for the display module 21 based thereon. The target color display mode corresponds to color vision sensitivity information of the user of the augmented reality device.

The control device may query the preset data set to obtain the color vision sensitivity information corresponding to the acquired user's identity information, and judge whether the user is a color recognition disorder patient according to the color vision sensitivity information corresponding to the user's identity information. If the user is judged as a color recognition disorder patient, a personalized color display mode corresponding to the color vision sensitivity information is acquired.

Furthermore, the augmented reality device further comprises an identity information acquiring module 23. The identity information acquiring module 23 is configured to collect user's identity information. The collected identity information may be provided to the control device for querying for the color vision sensitivity information. In an embodiment, the identity information acquiring module 23 may collect the user's biometric data. Exemplarily, the identity information acquiring module 23 is an optical sensor or camera to collect for example iris or face images, etc. Additionally or alternatively, the identity information acquiring module 23 may also be a flat panel sensor for collecting fingerprints or palm prints and the like.

Furthermore, the augmented reality device further comprises a detection module 24. The detecting module 24 is configured to detect ambient brightness information and user's visual field environment color information. The detected ambient brightness information and user's visual field environment color information may be provided to the control device so that the control device may generate a compensation parameter for each sub-pixel of the image according to the color vision sensitivity information and the ambient brightness information and the user's visual field environment color information. A compensated data signal is generated by compensating for the data signal of each sub-pixel according to the compensation parameter of each sub-pixel. The display module 21 may employ a personalized color display mode to perform image display based on the compensated data signal.

Furthermore, the detection module 24 comprises an ambient brightness sensor 241 and a visual field environment color sensor 242. The ambient brightness sensor 241 is configured to sense the ambient brightness information. The visual field environment color sensor 242 is configured to sense the user's visual field environment color information. The visual field environment color sensor 242 may be a camera or a device with a camera.

Furthermore, the display module 21 is further configured to output, under the control of the control device, a plurality of options for personalized color display modes corresponding to the color vision sensitivity information, so that the user judges whether the plurality of options comprise the personalized color display mode desired by the user. If yes, the user determines a personalized color display mode from the plurality of personalized color display modes corresponding to the color vision sensitivity information; if not, the display module 21 outputs, under the control of the control device, another plurality of options of personalized color display modes corresponding to the color vision sensitivity information, for the user to continue to perform the judgment. Optionally, the display module 21 may output a plurality of color mode pictures. These color mode pictures correspond to options for respective personalized color display modes. In an embodiment, the user may select a personalized color display mode from a plurality of options for personalized color display modes corresponding to the color vision sensitivity information by means of touch when viewing the color mode picture.

In an exemplary embodiment, the display module 21 may also perform display based on the compensated data signal from the control device.

In an exemplary embodiment, the identity information acquiring module 23 may further provide the collected user's identity information to the control device so as to query for the color vision sensitivity information.

In an exemplary embodiment, the ambient brightness detection module 241 and the visual field environment detection module 242 may also provide the detected brightness information and color information to the control device for compensation of the data.

Figure 6:
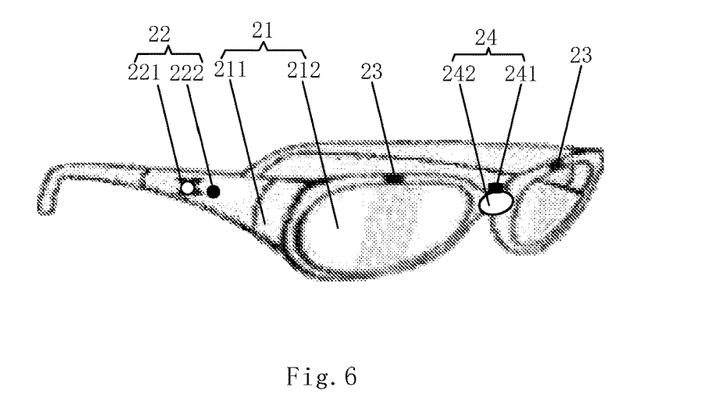
FIG. 6 is a schematic diagram of another augmented reality device according to an exemplary embodiment.
Figure 7:
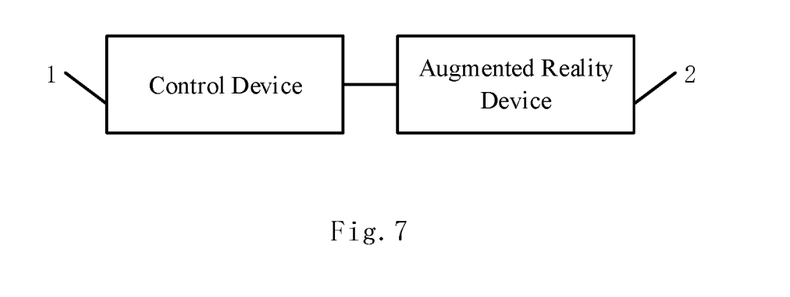
FIG. 7 is a schematic structural diagram of an augmented reality processing system according to an exemplary embodiment.

FIG. 6 is a schematic diagram of another augmented reality device according to an exemplary embodiment. As shown in FIG. 6, the augmented reality device comprises a body 21 and a display assembly 22. The display assembly 22 comprises a display module 221 and a display mode setting module 222.

In an exemplary embodiment, the augmented reality device is an AR glasses, and the body 21 comprises a glasses frame 211 and lenses 212 disposed on the glasses frame 211. The display module 221, the display mode setting module 222, the identity information acquiring module 23 and the detection module 24 are all placed on the glasses frame 211.

Optionally, the display module 221 and the display mode setting module 222 may be located inside the glasses frame 211. Exemplarily, the display module 221 may be located inside legs of the glasses frame 211. Although not shown, it would be understood that, in practical application, the display module 221 and the display mode setting module 222 may optionally be located external of the glasses frame 211 or at any other suitable position of the body 21.

Optionally, the identity information acquiring module 23 is located external of the glasses frame 211. The number of identity information acquiring modules 23 may be two. Each identity information acquiring module 23 is located on a lens rim of the glasses frame 211. The lens is placed in the lens rim. In an embodiment, the user's identity information comprises the user's iris information. Optionally, the identity information acquiring module 23 may comprise a camera or a device with a camera, and the camera directly acquires the user's human eye pupil pattern to identify the user's iris information.

Optionally, in practical application, the identity information acquiring module 23 may also be disposed inside the glasses frame 211. At this time, the identity information acquiring module 23 may employ the same optical path as AR virtual display to obtain the user's human eye iris pattern to recognize the user's iris information. This case is not specifically shown in the figure. It will be appreciated that in some embodiments, the augmented reality device may further comprise a haptic interface or other accessory for use with the AR glasses, and the identity information acquiring module 23 may be disposed in such an interface or accessory.

Optionally, the detection module 24 is located external of the glasses frame 211. Exemplarily, the detection module 24 may be located at the bridge of the glasses frame 211.

Optionally, the display mode setting module 25 is located external of the glasses frame 211. In the technical solution of the augmented reality device provided by the embodiment, if it is determined according to the color vision sensitivity information that the user is a color recognition disorder patient, the image display is performed in a personalized color display mode corresponding to the color vision sensitivity information, thereby avoiding the situation that the color recognition disorder patient cannot recognize the AR information, and thereby improving the user's experience in use.

FIG. 6 is a schematic structural diagram of an augmented reality processing system according to an exemplary embodiment. As shown in FIG. 6, the system comprises the control device 1 according to an exemplary embodiment and the augmented reality device 2 according to an exemplary embodiment.

The control device 1 may be a control device described above with reference to FIG. 4. The augmented reality device 2 may be an augmented reality device described above with reference to FIG. 5. In an exemplary embodiment, the control device 1 and augmented reality device 2 may be communicatively coupled via various types of communication media. The control device 1 and the augmented reality device 2 may coordinate operations with each other. Coordination may involve one-way or two-way exchange of information. For example, a component may communicate information in the form of a signal communicated over a communication medium. However, additional exemplary embodiments may alternatively utilize data messages. Such data messages may be sent across various connections. Exemplary connections comprise parallel interfaces, serial interfaces, and bus interfaces.

According to another exemplary embodiment, the control device may also be integrated into an augmented reality device. The augmented reality device according to this embodiment may comprise a control device according to an embodiment of the present disclosure and a display module for displaying an image in a color display mode. The color mode acquiring module sets a color display mode for the display module based on the target color display mode.

In a solution of the augmented reality processing system provided by the exemplary embodiment, the image display is performed by using a personalized color display mode corresponding to the color vision sensitivity information when determining that the user is a color recognition disorder patient according to the color vision sensitivity information, thereby avoiding the situation that the color recognition disorder patient cannot recognize the AR information, and thereby improving the user's experience in use.

"Modules", "devices" and the like in various embodiments may be implemented by using hardware units, software units, or a combination thereof. Examples of hardware units may comprise devices, components, processors, microprocessors, circuits, circuit elements (e.g., transistors, resistors, capacitors, inductors, etc.), integrated circuits, application-specific integrated circuits (ASICs), programmable logic Devices (PLDs), digital signal processors (DSPs), field programmable gate arrays (FPGAs), memory cells, logic gates, registers, semiconductor devices, chips, microchips, chipsets, and so on. Examples of software units may comprise software components, programs, applications, computer programs, application programs, system programs, machine programs, operating system software, middleware, firmware, software modules, routines, subroutines, functions, methods, processes, software interfaces, application programming interfaces (API), instruction sets, calculation codes, computer codes, code segments, computer code segments, words, values, symbols, or any combinations thereof. Determining whether an embodiment is implemented by using hardware units and/or software units may vary depending on any number of factors, such as desired computation rate, power level, heat resistance, processing period budget, input data rate, output data rate, memory resources, data bus speeds, and other design or performance constraints that are desirable for a given implementation.

Certain exemplary embodiments may comprise articles of manufacture. The articles of manufacture may comprise a storage medium for storing logic. Examples of storage media may comprise one or more types of non-transitory computer-readable storage media capable of storing electronic data, comprising volatile or nonvolatile memory, removable or non-removable memory, erasable or non-erasable memory, writable or rewritable memory, and so on. Examples of logic may comprise various software elements, such as software components, programs, applications, computer programs, application programs, system programs, machine programs, operating system software, middleware, firmware, software modules, routines, subroutines, functions, methods, processes, software interfaces, application programming interface (API), instruction sets, calculation codes, computer codes, code segments, computer code segments, words, values, symbols, or any combinations thereof. In one embodiment, for example, an article of manufacture may store executable computer program instructions that, when executed by a computer, cause the computer to perform the methods and/or operations in accordance with the described embodiments. The executable computer program instructions may comprise any suitable type of code, such as source code, compiled code, interpreted code, executable code, static code, dynamic code, and the like. The executable computer program instructions may be implemented in a predefined computer language, manner, or grammar for instructing a computer to perform certain functions. Instructions may be implemented using any suitable high-level, low-level, object-oriented, visual, compiled, and/or interpreted programming language.

Some embodiments may be described using the expressions "one embodiment," "an exemplary embodiment," or "an embodiment" along with their derivatives. These terms mean that specific feature, structures or properties described in conjunction with the embodiment are comprised in at least one embodiment. The phrases "in an embodiment" appearing places of the present disclosure do not necessarily all refers to the same embodiment.

It may be appreciated that the above embodiments are merely exemplary embodiments employed to explain the principles of the present disclosure, but the present disclosure is not limited thereto. Various modifications and improvements may be made by those having ordinary skill without departing from the spirit and scope of the disclosure, and such modifications and improvements are also considered to be within the scope of the disclosure.

The invention claimed is:

1. A method for controlling display of an augmented reality device, comprising:
   querying, by a control device, a preset data set to obtain color vision sensitivity information corresponding to acquired identity information of a user of the augmented reality device;
   judging, by the control device, whether the user is a color recognition disorder patient according to obtained color vision sensitivity information;
   acquiring, by the control device, a personalized color display mode corresponding to the color vision sensitivity information as a target color display mode when the user is judged as a color recognition disorder patient; and
   providing, by the control device, the augmented reality device with the target color display mode so that the augmented reality device employs the target color display mode to display an image and the displayed image comprises virtually-displayed content;
   wherein before providing the augmented reality device with the target color display mode, the method further comprises:
      acquiring ambient brightness information and user's visual field environment color information detected by the augmented reality device;
      generating a compensation parameter for each sub-pixel in the image according to the color vision sensitivity information, the ambient brightness information and the user's visual field environment color information so as to increase contrast between colors of the virtually-displayed content that is a foreground and colors of the user's visual field environment that is a background,
      performing compensation for a data signal of each sub-pixel according to the compensation parameter of each sub-pixel, and generating a compensated data signal; and providing the compensated data signal together with the target color display mode to the augmented reality device so that the augmented reality device employs the target color display mode to display the image based on the compensated data signal.

2. The method according to claim 1, wherein before querying, the method further comprises:
acquiring, by the control device, the user's identity information collected by the augmented reality device; and
querying, by the control device, to determine whether the preset data set comprises the collected user's identity information; and
querying, by the control device, the preset data set to obtain the color vision sensitivity information corresponding to the collected user's identity information when the collected user's identity information is comprised.

3. The method according to claim 2, further comprising:
initiating, by the control device, a color vision sensitivity test on the user when the collected user's identity information is not comprised in the preset data set, so as to obtain the color vision sensitivity information corresponding to the user's identity information; and
judging, by the control device, whether the user is a color recognition disorder patient based on the color vision sensitivity information resulting from the test.

4. The method according to claim 3, further comprising: storing, by the control device, the collected user's identity information in association with the color vision sensitivity information resulting from the test into the data set.

5. The method according to claim 1, wherein the generating a compensation parameter for each sub-pixel comprises:
generating, by the control device, a data signal target value for each pixel in the image according to the color vision sensitivity information, the ambient brightness information and the user's visual field environment color information, each pixel comprising a plurality of sub-pixels; and
generating, by the control device, a compensation parameter for each sub-pixel according to the data signal target value of each pixel.

6. The method according to claim 1, wherein the acquiring a personalized color display mode corresponding to the color vision sensitivity information comprises:
instructing, by the control device, the augmented reality device to output a plurality of options for personalized color display modes corresponding to the color vision sensitivity information, to enable the user to determine whether the plurality of options comprise a personalized color display mode desired by the user; if yes, acquiring the personalized color display mode determined by the user; and if no, instructing, by the control device, the augmented reality device to output another plurality of options for personalized color display modes corresponding to the color vision sensitivity information, to enable the user to continue to perform the determining.

7. The method according to claim 1, further comprising:
acquiring, by the control device, a standardized color display mode corresponding to the color vision sensitivity information as the target color display mode when the user is not judged as a color recognition disorder patient.

8. A computer storage medium comprising instructions which, when executed by a processor, enable the processor to implement the method according to claim 1.

9. A control device, comprising:
a query device implemented by a hardware unit and configured to query a preset data set to obtain color vision sensitivity information corresponding to acquired identity information of a user of an augmented reality device;
a judger implemented by a hardware unit and configured to judge whether the user is a color recognition disorder patient according to obtained color vision sensitivity information;
a color mode acquirer implemented by a hardware unit and configured to acquire a personalized color display mode corresponding to the color vision sensitivity information as a target color display mode when the judger judges that the user is a color recognition disorder patient, and provide the augmented reality device with the target color display mode so that the augmented reality device employs the target color display mode to display an image and the displayed image comprises virtually-displayed content; and
a compensator implemented by a hardware unit and configured to generate a compensation parameter for each sub-pixel in the image according to the color vision sensitivity information and ambient brightness information and user's visual field environment color information detected by the augmented reality device so as to increase contrast between colors of the virtually-displayed content that is a foreground and colors of the user's visual field environment that is a background; perform compensation for a data signal of each sub-pixel according to the compensation parameter for each sub-pixel to generate a compensated data signal; and provide the compensated data signal together with the target color display mode to the augmented reality device, so that the augmented reality device employs the target color display mode to display the image based on the compensated data signal.

10. The control device according to claim 9, wherein the query device is further configured to acquire the user's identity information collected by the augmented reality device, query to determine whether the preset data set comprises the collected user's identity information, and query the preset data set to obtain the color vision sensitivity information corresponding to the collected user's identity information when the collected user's identity information is comprised.

11. The control device according to claim 10, wherein the query device initiates a color vision sensitivity test on the user when the collected user's identity information is not comprised, to obtain the color vision sensitivity information corresponding to the user's identity information; and the judger is further configured to judge whether the user is a color recognition disorder patient based on the color vision sensitivity information resulting from the test.

12. An augmented reality processing system, comprising:
the control device according to claim 9; and
an augmented reality device, comprising:
a display configured to display an image in a color display mode, a displayed image comprising the virtually-displayed content; and
a display mode setter implemented by a hardware unit and configured to set a color display mode for the display, the color display mode comprising at least one personalized color display mode in a case where a user of the augmented reality device is a color recognition disorder patient and a standard color display mode in a case where the user is a normal color recognizer;

wherein the display mode setter is configured to receive a target color display mode from the control device and set it as a color display mode for the display, the target color display mode corresponding to color vision sensitivity information of the user of the augmented reality device and the display is further configured to employ the received target color display mode to display the image based on the compensated data signal based on the compensated data signal.

13. An augmented reality device, comprising:
the control device according to claim 9; and
a display for displaying an image in a color display mode, a displayed image comprising the virtually-displayed content;
wherein the color mode acquirer sets the color display mode for the display based on the target color display mode and the display is further configured to employ the received target color display mode to display the image based on the compensated data signal based on the compensated data signal.

14. An augmented reality device, comprising:
a display configured to display an image in a color display mode, a displayed image comprising virtually-displayed content;
a display mode setter implemented by a hardware unit and configured to set a color display mode for the display, the color display mode comprising at least one personalized color display mode in a case where a user of the augmented reality device is a color recognition disorder patient and a standard color display mode in a case where the user is a normal color recognizer; and
a detector configured to detect ambient brightness information and user's visual field environment color information, and provide the detected information to a control device so that the control device generates a compensated data signal for each sub-pixel of the image based on the color vision sensitivity information and the ambient brightness information and the user's visual field environment color information so as to increase contrast between colors of the virtually-displayed content that is a foreground and colors of the user's visual field environment that is a background;

wherein the display mode setter is configured to receive a target color display mode from the control device and set it as a color display mode for the display, the target color display mode corresponding to color vision sensitivity information of the user of the augmented reality device, and the display is further configured to employ the received target color display mode to display the image based on the compensated data signal based on the compensated data signal from the control device.

15. The augmented reality device according to claim 14, further comprising an identity information acquirer implemented by a hardware unit and configured to collect user's identity information, and provide the collected user's identity information to the control device, so that the control device, based on the collected user's identity information, queries for the color vision sensitivity information corresponding thereto.

16. The augmented reality device according to claim 15, including augmented reality glasses as a body, the augmented reality glasses comprising a glasses frame and lenses disposed on the glasses frame,
wherein the display, the display mode setter, the identity information acquirer and the detector are all placed on the glasses frame.

17. The augmented reality device according to claim 14, wherein the detector comprises:
an ambient brightness sensor configured to sense the ambient brightness information; and
a visual field environment color sensor configured to sense the user's visual field environment color information.

* * * * *